United States Patent [19]

Mueller et al.

[11] Patent Number: 5,041,089
[45] Date of Patent: Aug. 20, 1991

[54] VASCULAR DILATION CATHETER CONSTRUCTION

[75] Inventors: Richard L. Mueller, Mountain View; Gerri Chatelain, Pleasanton; Richard Jaraczewski, Livermore, all of Calif.

[73] Assignee: Devices for Vascular Intervention, Inc., Redwood City, Calif.

[21] Appl. No.: 242,012

[22] Filed: Sep. 8, 1988

Related U.S. Application Data

[63] Continuation-in-part of Ser. No. 131,775, Dec. 11, 1987, abandoned.

[51] Int. Cl.⁵ ............................................. A61M 25/00
[52] U.S. Cl. ...................................... 604/96; 604/103; 604/280; 606/7; 606/194
[58] Field of Search ............... 604/20, 96-103, 604/264, 271, 280; 606/7, 192, 194; 128/395, 398, 401

[56] References Cited

U.S. PATENT DOCUMENTS

| | | |
|---|---|---|
| 3,911,927 | 10/1975 | Rich et al. |
| 4,195,637 | 4/1980 | Gruntzig et al. |
| 4,323,071 | 4/1982 | Simpson et al. |
| 4,445,892 | 5/1984 | Hussein et al. ............ 604/101 |
| 4,448,188 | 5/1984 | Loeb ........................ 128/6 |
| 4,470,407 | 9/1984 | Hussein .................... 128/6 |
| 4,479,497 | 10/1984 | Fogarty et al. |
| 4,526,175 | 7/1985 | Chin et al. |
| 4,624,657 | 11/1986 | Gould et al. |
| 4,754,752 | 7/1988 | Ginsburg et al. |
| 4,775,371 | 10/1988 | Mueller, Jr. |
| 4,787,388 | 11/1988 | Hofmann ................. 606/194 |
| 4,817,613 | 4/1989 | Jaraczewski et al. |
| 4,834,093 | 5/1989 | Littleford et al. ......... 606/194 |
| 4,863,424 | 9/1989 | Blake, III et al. ........ 604/103 |
| 4,878,492 | 11/1989 | Sinofsky ................. 128/395 |

FOREIGN PATENT DOCUMENTS

| | | | |
|---|---|---|---|
| 182689 | 5/1986 | European Pat. Off. ..... 604/96 |
| WO87/00442 | 1/1987 | PCT Int'l Appl. . |
| 89/05165 | 6/1989 | PCT Int'l Appl. ......... 604/103 |

OTHER PUBLICATIONS

Sanborn et al., (1985), J. Am. Col. Cardiol. 5: 934-938.
Welch et al., (1987), Circulation 76: 1353-1363.
Lee et al., (1987), Am. Heart J. 113: 1507-1508; 114: 1524-1526.
Spears (1987), Am. J. Cardiol. 61B-64B.
Spears (1986), Cardiovasc. Intervent. Radiol. 9: 303-312.
Hiehle, Jr. et al., (1985), Am. J. Cardiol. 56: 953-957.

*Primary Examiner*—Stephen C. Pellegrino
*Assistant Examiner*—Ralph A. Lewis
*Attorney, Agent, or Firm*—Townsend and Townsend

[57] ABSTRACT

An improved vascular dilation catheter comprises an involuted tubular structure including outer and inner tubular walls which extend the entire length of the catheter. The outer tubular wall is enlarged at a distal end of the catheter to form a dilation balloon, and extends back the remaining length of the flexible tube at a reduced diameter to define an annular lumen which is used to inflate the balloon. Alternatively, the outer tubular wall may conform to the exterior of the inner tubular wall and separate axial lumens may be provided for inflation. By providing means for heating inflation medium within the balloon, the catheter may be utilized for performing thermal ablation therapy.

21 Claims, 4 Drawing Sheets

VASCULAR DILATION CATHETER CONSTRUCTION

The present application is a continuation-in-part of application Ser. No. 131,775 filed on Dec. 11, 1987, now abandoned the entire disclosure of which is incorporated herein by reference.

BACKGROUND OF THE INVENTION

1. Field of the Invention

The present invention relates generally to the construction of dilation catheters for angioplastic treatment of obstructed blood vessels, and more particularly to an improved catheter construction wherein a sheath envelopes a flexible catheter tube to define both a dilation balloon at a distal end of the tube and an annular lumen connecting the balloon to a proximate end of the tube.

Balloon angioplasty was first described by Andreas Gruntzig in 1977. Dr. Gruntzig employed a balloon-tipped flexible catheter to percutaneously dilate a region of stenosis within the coronary artery of a patient with atherosclerotic coronary artery disease. Since the original work, the use of percutaneous balloon angioplasty has become widespread, with treatment of occluded peripheral blood vessels as well as coronary arteries.

A common type of dilation catheter consists of a pair of coaxial tubes which are sealed together at a distal end. The outer tube is expanded to form a balloon near a distal end of the catheter and a narrow annular lumen extends from the balloon to a proximate end. A fitting is secured to the proximate end, allowing for the infusion of an inflation medium through the annular lumen to the balloon. The catheter may be inserted over a guidewire to the desired location within a blood vessel, and inflated to dilate a stenosed region by now well known techniques.

The dilation catheter construction just described suffers from several drawbacks. In particular, the need to seal the outer tube to the inner catheter tube limits the choice of materials available for both tubes. For example, cross-linked polyolefins and halocarbon polymers, which are desirable as the material for the outer tube which defines the balloon, are difficult to bond to other materials suitable for the inner tube. Thus, most coaxial balloon catheters either avoid the use of such materials, compromise on the material used for the inner tube, or provide elaborate means for sealing the distal end. Second, even when compatible materials are chosen, the seam at the bonded end will be subject to failure when the catheter is use. Inflation pressures on the order of 80 to 260 psi are common, and bursting of the catheter could result in serious complications. Third, coaxial catheter constructions have typically included a rigid segment having a length on the order of 1 cm at the distal tip of the catheter. Such a rigid tip can, when the adjacent balloon is inflated, be pressed against the vessel wall. During the treatment of particularly tortuous vessels and/or with very high dilation pressures, the rigid tip can sometimes puncture the vessel wall. Finally, the construction methods employed in fabricating conventional dilation catheters are problematic and time consuming, increasing both the cost of production and the difficulty of meeting product specifications.

As an alternative to balloon angioplasty, various approaches have been proposed for the thermal ablation of vascular obstructions, including the use of direct laser radiation and heated contact elements. Although such techniques would be free from certain drawbacks of conventional balloon angioplasty, including restenosis and abrupt reclosure of the blood vessel, they suffer from their own disadvantages. Specifically, direct laser radiation can accidentally pierce the blood vessel wall, and it is often difficult to contact a heated element against the desired region of stenosis, particularly when the stenosis is non-uniformly distributed around the blood vessel.

Heating the inflation medium within balloons has been proposed as a method for remolding dissections which occur during conventional angioplasty, causing restenosis and abrupt reclosure. Heating for such remolding generally is carried out at lower temperatures than for ablation.

It would therefore be desirable to provide improved dilation catheters and methods for fabricating dilation catheters which do not require bonding between an inner tube and an outer tube, as described above, and which are free from rigid sealing segments at their distal ends. Moreover, it would be desirable that such methods allow for a wider selection of catheter materials and simplify the fabrication process to both reduce the cost of the process and provide for improved product quality. In particular, it would be desirable if such dilation catheters could be used in methods for the thermal ablation of vascular obstructions where the inflation medium within the balloon is heated to relatively high temperatures.

2. Description of the Background Art

The basic technique of balloon angioplasty is taught in U.S. Pat. No. 4,195,637. U.S. Pat. No. 4,323,071 and PCT Patent WO 87/00442 each describe the construction of coaxial balloon-tipped dilation catheters of the type described above. The use of direct laser energy for ablating stenosis is described in U.S. Pat. Nos. 4,445,892 and 4,448,188, and Sanborn et al. (1985) J. Am. Col. Cardiol. 5:934–938. Ablation of stenosis using a laser-heated metallic cap is described in Welch et al. (1987) Circulation 76:1353–1363, Sanborn et al. (1985) supra., and Lee et al. (1987) Am. Heart J. 113:1507–1508 and 114:1524–1526. The use of direct laser energy for the fusion of tissue dissected during balloon angioplasty is suggested in Spears (1987) Am. J. Cardiol. 61B–64B; Spears (1986) Cardiovasc. Intervent. Radiol. 9:303–312; and Hiehle, Jr., et al. (1985) Am. J. Cardiol. 56:953–957. U.S. Pat. No. 4,470,407 describes an endoscope which employs a laser-illuminated balloon. U.S. Pat. No. 4,754,752 describes a balloon catheter having a metal block heated by laser energy for convectively heating inflation medium within the balloon.

SUMMARY OF THE INVENTION

According to the present invention, improved vascular dilation catheters are constructed by a novel fabrication method. Specifically, the vascular dilation catheters comprise a continuous, involuted structure including outer and inner tubular walls which are joined without seams at a distal end thereof. The outer tubular wall is expanded near the distal end to define the dilation balloon. Optionally, the inner tubular wall further includes a separate flexible reinforcement tube with a sheath extending over both the internal and external surfaces of the reinforcement tube to complete the involuted structure. The sheath is folded over a distal end of the flexible reinforcement tube and is expanded at or near the distal end to define a dilation balloon.

The entire dilation balloon is thus completely free from seams and seals which are subject to failure and limit the choice of usable materials. In particular, there is no rigid sealing segment at the distal end of the catheter as has been previously required in most other balloon catheter constructions. Moreover, the fabrication method is particularly convenient, inexpensive, and provides very high product quality.

In a first preferred embodiment, the outer tubular wall is spaced-apart from the external surface of the inner tubular wall to define an annular lumen along the entire length from the balloon to the proximate end of the catheter. The annular lumen provides an inlet conduit for inflation medium from the proximate end of the catheter to the balloon.

In a second preferred embodiment, the outer tubular wall conforms tightly about the external surface of the inner tubular wall except at the distal end where the balloon is formed. The catheter includes at least one lumen, and usually two or more lumens, extending its entire length to provide inflation access at the proximate end. In a third preferred embodiment, the outer tubular wall conforms about the catheter tube, and at least one lumen is formed in the sheath or flexible reinforcement tube to provide inflation access.

A particularly convenient and efficient method is provided for fabricating the vascular dilation catheters of the present invention. An elongate tubular member is first formed by extrusion of a suitable thermoplastic, usually a cross-linked polyolefin or halocarbon (usually fluorocarbon) polymer. Depending on the particular design, one or more axial lumens may be formed within the tube wall to extend from a proximate end of the tubular member to the location where the balloon will subsequently be formed. A preselected length of the tubular member, usually about half, will then be expanded and rolled back over the remaining length to form the basic involuted structure of the catheter. The balloon can then be formed by further expanding the distal end of the outer tubular wall. Frequently, it will be desirable to provide the inner tubular wall with a greater thickness in order to enhance the mechanical strength of the catheter.

When the elongate tubular member is formed from a low strength material, such as a polyolefin, it will usually be desirable to provide a separate flexible reinforcement tube member to enhance the mechanical strength of the catheter. The elongate tubular member then acts as the sheath, as described above. Such a structure is formed by extruding the flexible reinforcement tube over the sheath from one end to the location where the balloon will be formed. The flexible reinforcement tube may include one or more lumens extending from the proximate end to the balloon location, again depending on the particular design being fabricated. The reinforcement tube material covers only a portion of the sheath, and the exposed segment of the sheath is then expanded to an inside diameter greater than the outside diameter of the reinforcement tube. By folding the sheath back over the exterior of the flexible reinforcement tube, a tri-layer construction comprising an inner sheath layer, a flexible tube layer, and an outer sheath layer is formed, where the inner sheath layer and flexible tube layer together define the inner tubular wall while the outer sheath layer defines the outer tubular wall. The outer sheath layer is then shrunk to a preselected diameter over a first portion of the tube extending from the proximate end to a point spaced inward from the distal end. The portion of the sheath which has not been shrunk defines the dilation balloon, while the shrunken portion either conforms to the catheter tube or defines the annular inflation lumen. To form the annular lumen, a temporary blocking tube is placed over the catheter tube during shrinkage of the sheath.

The balloon catheters of the present invention may further include means for heating the inflation medium within the dilation balloon or directly heating the stenosis through the balloon wall in order to perform thermal ablation angioplasty. By employing high temperature thermoplastics, particularly fluorocarbon polymers, as the catheter materials, balloon structures capable of operating at the high temperatures required for ablation therapy may be provided. Such heated balloons are generally free from the disadvantages associated with other thermal ablation techniques, as described above.

DESCRIPTION OF THE SPECIFIC EMBODIMENTS

Figure 1:
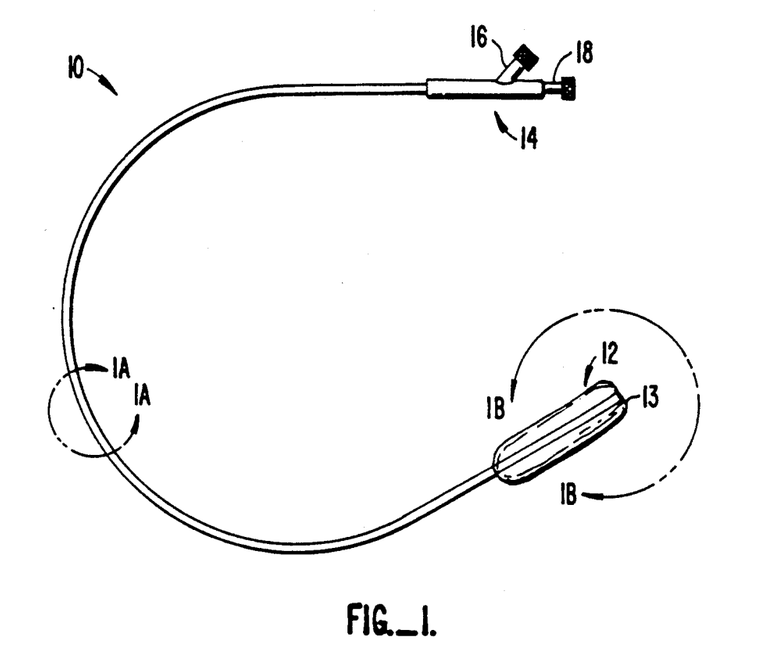
FIGS. 1, 1A, and 1B illustrate a first preferred embodiment of a vascular dilation catheter constructed in accordance with the principles of the present invention.

Referring now to FIG. 1, a first vascular dilation catheter 10 constructed in accordance with the principles of the present invention will be described. The first catheter 10 is of the type including an annular lumen providing inflation access to a dilation balloon. The catheter 10 includes a dilation balloon tip 12 at its distal end and a manifold fitting 14 at its proximate end. The manifold fitting 14 includes a side port 16 for the introduction of inflation medium to the catheter and an axial port 18 for insertion of the catheter 10 over a conventional guidewire (not illustrated). Additional ports (not illustrated) may be provided in the manifold 14 for other connections to the catheter 10, such as a perfusate connection, a bleed line connection permitting the discharge of air from the balloon as it is filled with inflation medium, and the like. Such connections are well known and their incorporation in the catheters of the present invention would be a matter of routine to one skilled in the art.

Figure 1A:
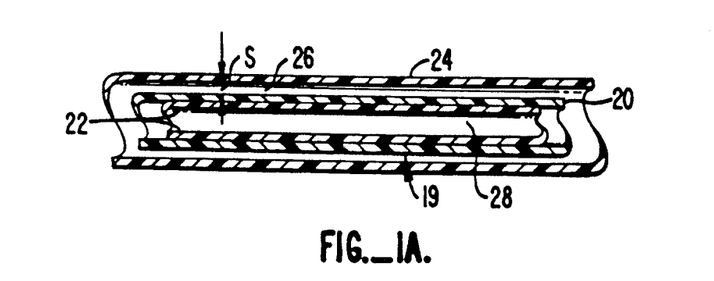

The main body of the vascular dilation catheter 10 comprises a three-layer structure best observed in FIG. 1A. An inner tubular wall 19 includes a flexible reinforcement tube 20 formed over an inner sheath 22, as will be described in more detail hereinafter. An outer tubular wall or sheath 24 circumscribes the flexible tube 20 and is spaced-apart therefrom to define an annular lumen 26 which extends the length of the catheter from the balloon tip 12 to the manifold fitting 14. A central lumen 28 also extends the entire length of the catheter 10 from the balloon tip 12 to the fitting 14. The side port 16 of fitting 14 is fluidly connected to the annular lumen 26 to provide for introduction of inflation medium to the balloon 12, while axial port 18 is sealingly connected to the inner lumen 28 to allow for insertion of the catheter 10 over a guidewire (not illustrated).

Figure 1B:
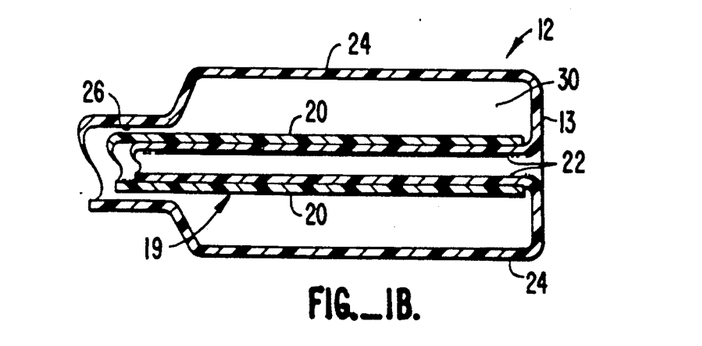
Figure 2:
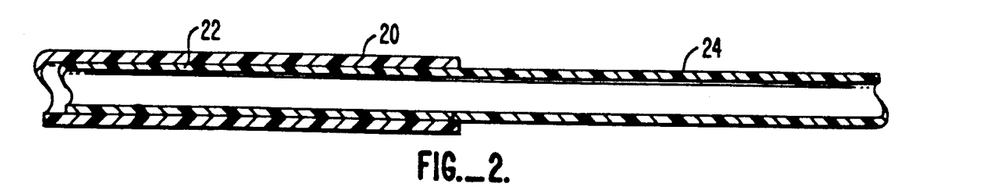
FIGS. 2-5 illustrate steps of the method for fabricating vascular dilation catheters according to the present invention.

As best observed in FIG. 1B, the balloon tip 12 is defined by the inner sheath 22 extending out of the open end of flexible reinforcement tube 20 and folding back over the exterior surface of said tube so that it becomes outer tubular wall 24 (which is a continuous extension of inner sheath 22). The diameter of the outer wall or sheath 24 at the distal end of catheter 10 is substantially greater than that over the remaining length of the catheter so that it defines the dilation balloon 12. The internal volume 30 of the dilation balloon 12 forms a continuous volume with the annular lumen 26 which extends through the remaining length of the catheter 10 to the manifold fitting 14. Thus, inflation fluid which is introduced through port 16 of fitting 14 will eventually reach the interior volume 30 of the balloon 12.

The advantages of the catheter 10 of the present invention arise from the fact that the balloon 12 is an integral portion of the sheaths 22 and 24. Thus, the balloon 12 is not sealed to the catheter at all and, in fact, the only sealing required for the catheter may be provided at the fitting 14. Moreover, the sheath 22 and 24 is a continuous piece of material entirely free from seams which are prone to failure and difficult to form. It is a particular advantage that the balloon 12 terminates in a substantially flat or blunt face 13 and is free from the protruding seals which characterized the prior art. Such rigid seals presented a danger of puncturing the wall of the blood vessel being treated, as described above.

The dimensions of the vascular dilation catheter 10 will vary depending on the particular use. For peripheral arteries, the catheters 10 will generally have a length in the range from about 40 to 150 centimeters, with lengths from about 40 to 90 centimeters being generally suitable for peripheral arteries and lengths from about 115 to 150 centimeters being generally suitable for coronary arteries. The outside diameter of the catheter (excluding the balloon tip 12) will generally vary from about one-half to two millimeters, with catheters for peripheral arteries generally being larger. The balloon tip 12 will have a length typically in the range from about one to twenty centimeters, and a diameter when fully inflated in the range from about one to 30 millimeters, with diameters from one to ten millimeters being suitable for vascular dilation and larger balloons being suitable for dilation of coronary valves.

The flexible reinforcement tube 20 will have an outside diameter which is somewhat smaller than the inside diameter of the outer tubular wall or sheath 24. Typically, the spacing between the outer wall or sheath 24 and the reinforcement tube 20 (dimension "S" in FIG. 1A) will be in the range from about 0.05 to 0.6 mm. The outside diameter of the inner sheath 22 conforms precisely to the inside diameter of the flexible reinforcement tube 20, while the central lumen has a diameter in the range from about 0.25 to 1.50 mm. Typically, the wall thickness of both the inner and outer sheaths 22 and 24 will be in the range from about 0.05 to 0.25 mm, while the wall thickness of the flexible reinforcement tube 20 will be in the range from 0.05 to 0.5 mm.

Referring now to FIGS. 2-5, a method for fabricating vascular dilation catheters 10 according to the principles of the present invention will be described. Heat-shrinkable plastic tubing is provided in a length which is approximately twice that of the desired catheter length. The tubing, which subsequently forms both the inner sheath 22 and outer tubular wall or sheath 24, is supported while flexible reinforcement tube 20 is formed thereover, typically by conventional extrusion and/or braiding processes. The flexible reinforcement tube 20 should cover approximately one-half of the length of the sheath material 22/24. That is, the length of the tube 20 will correspond to the desired length of the catheter 10. To that end, the flexible reinforcement tube 20 may be extruded to the proper length, or may be extruded over a greater length of the sheath 22/24 and then peeled back to the proper length.

Suitable heat-shrinkable materials include cross-linked polyolefins, such as polyethylenes, polypropylenes, polyisoprenes; halocarbon polymers, particularly fluorocarbon polymers; and copolymers thereof. Such materials display strong plastic memory and may be shaped to a desired diameter when heated above their crystalline melting points. If held in shape while cooled, the polyolefin and halocarbon materials will retain their shape indefinitely. On reheating above the crystalline melting point, however, the stressed portion will tend to return to the original shape when cross-linked. For use in the present invention, the sheath tubing 22/24 should initially be in an unstressed condition such that it will tend to return to its original diameter when heated.

Suitable materials for the flexible reinforcement tube 20 include a wide variety of thermoplastics and thermosetting plastics. Unlike certain prior art fabrication methods, the present invention does not require bonding compatibility between the flexible reinforcement tube 20 and the balloon (sheath) material since there will be no bonding in the process. Suitable materials include nylons, polyethylenes, polyolefins, polyvinylchlorides, polyurethanes, halocarbon polymers and the like. The use of polyurethanes is preferred as they are available with a wide variety of mechanical properties which allow the catheter to be tailored to a particular end use. Also suitable are various fiber-reinforced composite materials and braided constructions where a metal braid core is coated with a suitable resin, particularly epoxy and polyurethane resins. The construction of suitable braided catheter tubing is described in U.S. patent application Ser. No. 72,439, filed on June 9, 1987, for Guiding Catheter, the disclosure of which is incorporated herein by reference. Finally, multiple layer constructions including two or more of the materials just described may also find use. In a particular application, the flexible tubing may be reinforced in the region of the balloon 12 in order to prevent collapse of the central lumen 28 during inflation of the balloon.

Figure 3:
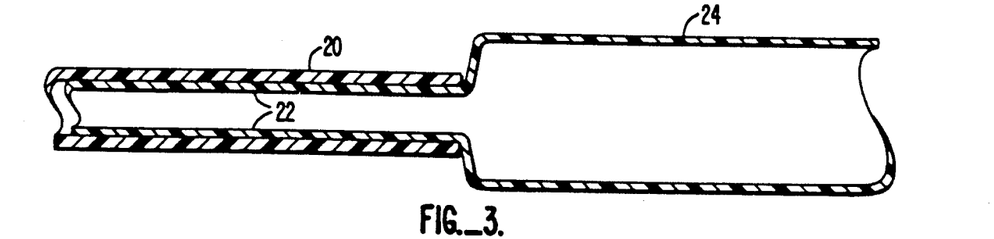

Referring now in particular to FIG. 3, after flexible reinforcement tube 20 has been formed over approximately one-half the length of the sheath material 22/24, the portion 24 of the sheath material which extends out of the end of tubing 24 is expanded to a diameter corresponding generally to the desired balloon diameter in the final catheter construction. Expansion is accomplished by heating the sheath material and expanding the walls, either by fluid (liquid or gas) pressure or placement over an appropriate mandrel. By cooling the sheath material while in this expanded condition, the shape will be retained indefinitely until the material is again heated.

Figure 4:
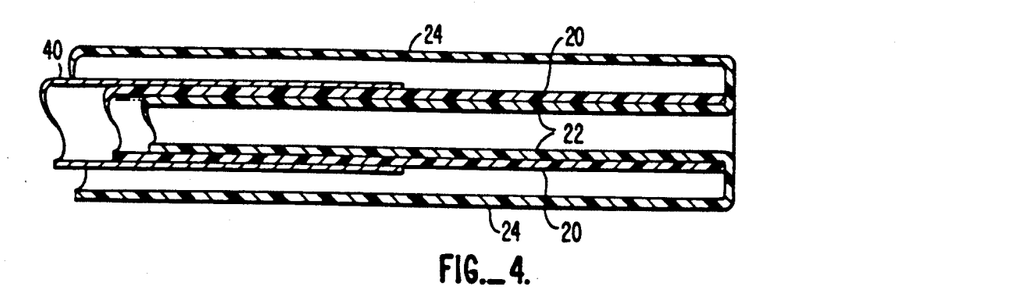
Figure 5:
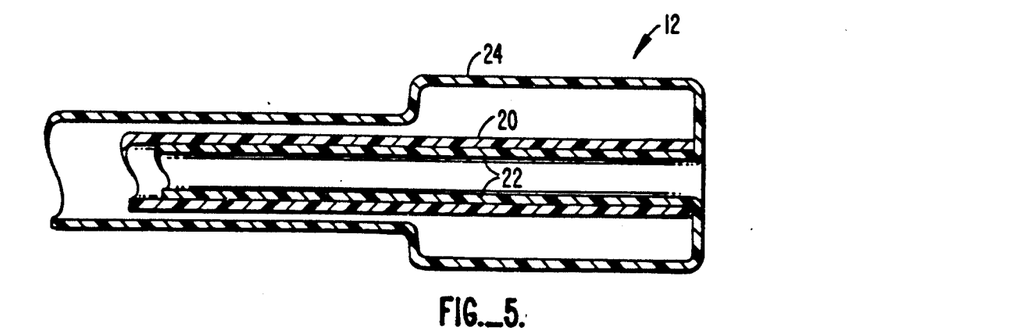

Referring now to FIG. 4, the outer sheath material 24 is next folded back over the flexible tube 20 so that the flexible reinforcement tube 20 is completely enveloped within the sheath material. A spacing mandrel 40 (typically formed from an adhesion-resistant material such as polytetrafluoroethylene available under the tradename Teflon ®) is next inserted over the flexible tube 20 extending at least until the point where it is desired to form the dilation balloon 12. The sheath material 24 is next heated along the length of the catheter, with the exception of the length where it is desired to form the balloon 12. By heating above the crystalline melting point for the material employed, the sheath material 24 will tend to shrink back to its original diameter. The spacing mandrel 40, however, prevents full shrinkage back and instead terminates the shrinkage at the desired inside diameter for the outer sheath wall 24. Once the desired diameter is reached, the material may again be cooled and the mandrel 40 removed. The final product, as illustrated in FIG. 5, is thus obtained.

After connection to a manifold fitting 14, as described previously, the catheters 10 of the present invention may be used in conventional vascular angioplastic techniques, such as those described in U.S. Pat. No. 4,323,071, the disclosure of which is incorporated herein by reference. Briefly, the catheter 10 will be located within the patient's vascular system by inserting the central lumen 28 over a guidewire (not illustrated). Once the dilation balloon 12 of the catheter 10 is properly located in a region of stenosis, the balloon 12 is inflated by introducing an inflation medium through port 16 of fitting 14. The inflation medium travels through the annular lumen 26 eventually reaching the internal volume 30 of the balloon 12. The balloon 12 is expanded one or more times for short periods of time until it appears that the stenosed region has been adequately enlarged.

Figure 6:
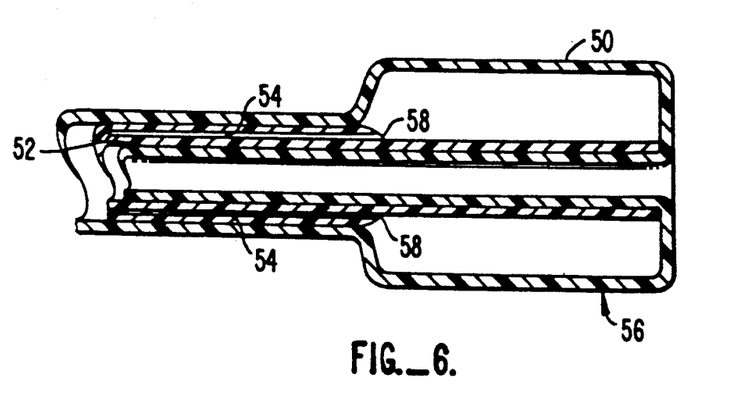
FIGS. 6, 7, and 8 illustrate alternate preferred embodiments of the vascular dilation catheter of the present invention.

Referring now to FIG. 6, a first alternative construction of the catheter of the present invention will be described. A sheath 50 is formed from the same materials and by the same methods as described above for sheath 22/24. A flexible reinforcement tube 52 is also formed from the same materials as described above for flexible reinforcement tube 20, and the tube will be extruded over the sheath and the sheath folded back in the same general manner as for the first embodiment. Flexible reinforcement tube 52, however, will include at least one, and usually a plurality of axial lumens 54 extending the entire length of the tube. The sheath 50 is shrunken to conform tightly to the flexible tube 52 along the entire length of the tube, except at the distal end where dilation balloon 56 is located. The lumens 54 terminate in ports 58 which open into the interior of the balloon 56. When multiple lumens 54 are employed, one or more of the lumens can be used to supply inflation medium while one or more of the remaining lumens are used to vent the balloon.

Figure 7:
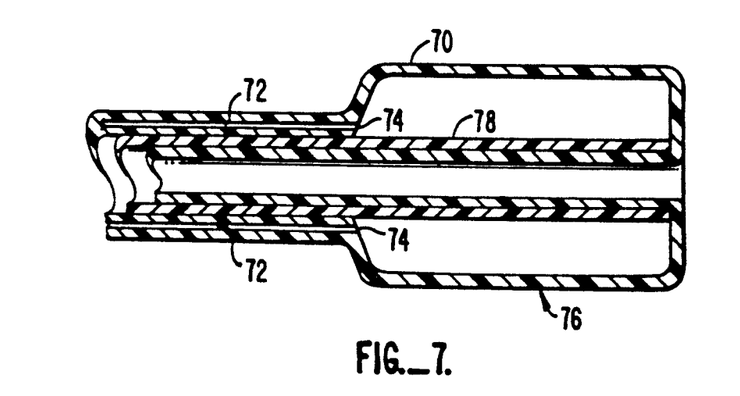

Referring now to FIG. 7, a second alternative construction of the catheter of the present invention will be described. A sheath 70 is formed from the same materials as described above for sheath 22/24. The method of formation of sheath 70 is also similar, except that a portion of the sheath length will have a somewhat greater wall thickness and one or more axial lumens 72 formed therein. The lumens 72 terminate in ports 74 which open into the interior of balloon 76. The balloon 76 is formed after the sheath 70 is folded back over flexible catheter tube 78 which is extruded over sheath 70 in the same manner as described for flexible reinforcement tube 20 above. The sheath 70 is then heat shrunk to conform tightly to the tube 78 to seal the balloon 76. Inflation access is provided by lumen(s) 74.

In the embodiments of both FIGS. 6 and 7, the dilation balloons 56 and 76, respectively, are sealed by heat shrinking the sheaths 50 and 70 to the flexible catheter tubes 52 and 78. Normally, the sheaths 50 and 70 will extend the entire length of the catheter providing an excellant seal with virtually no likelihood of failure. The seal, of course, need not extend the entire length of the catheter and it is necessary only that a sufficient seal length be provided to assure that there will be no leakage of the inflation media.

Figure 8:
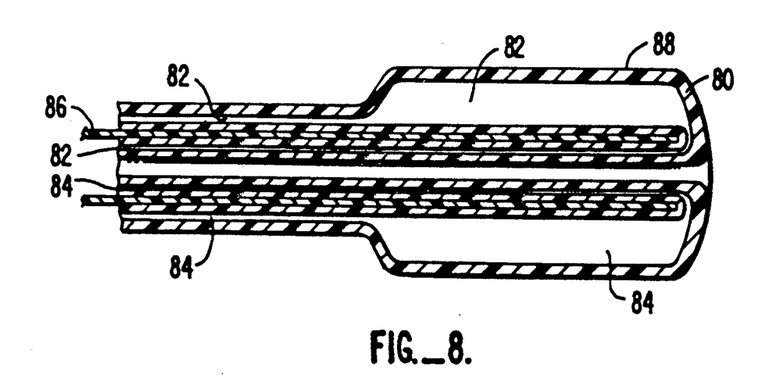

Referring now to FIG. 8, a third alternative construction of the catheter of the present invention is illustrated. A sheath 80 is formed from the same materials as described above for sheath 22/24. Sheath 80, however, includes at least two axial lumens 82 and 84 extending its entire length. Usually, the lumens 82 and 84 will be crescent-shaped and occupy a substantial portion of the cross-sectional area of the sheath, typically about 50% of the area, or more. A flexible catheter tube 86 is formed over a portion of the length of sheath 80, and the remaining length of sheath 80 folded back over the tube 86. The sheath 80 is then heat shrunk, except for the distal end 88 which remains expanded to define the dilation balloon. The interior of the balloon is formed by the expanded lumens 82 and 84, and inflation medium can be supplied through the remaining lengths of the lumens.

In another modification of the catheter 10, the central lumen 28 may be shrunk onto a guidewire to reduce the diameter. The catheter would then, of course, be limited to fixed or semi-fixed guidewire applications. Alternatively, it would be possible to attach a coiled spring to the flexible tube to provide a self-guiding catheter.

Figure 9:
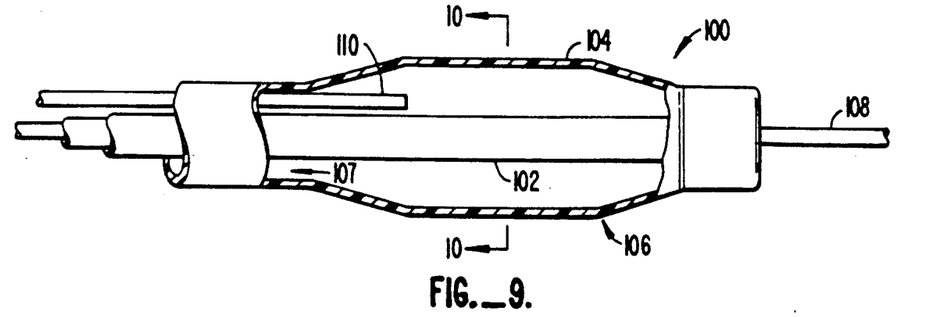
FIG. 9 illustrates a vascular catheter constructed in accordance with the principles of the present invention and having an optical waveguide for providing laser energy for heating inflation medium within a dilation balloon to perform thermal ablation angioplasty.
Figure 10A:
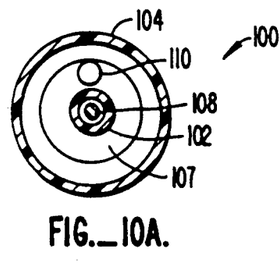
FIGS. 10A and 10B are alternative cross-sectional views taken along line 10-10 of FIG. 9.
Figure 10B:
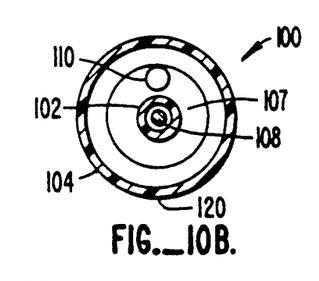

To this point, the catheter constructions described have all included an inner tubular wall including both a sheath layer and a reinforcement tube layer. Such two-layer constructions for the inner tubular wall, however, are not necessary and it is often desirable to fabricate catheters which include only a single layer of thermoplastic material which is folded back over itself to form the desired involuted structure of the present invention. Such single-layer constructions are particularly suitable when employing thermoplastics having a relatively high mechanical strength, such as halocarbon polymers, and the like. Referring now to FIGS. 9, 10A, and 10B, a catheter 100 which employs a single-layer construction will be described.

The catheter 100 is formed from a single tube of extruded thermoplastic material generally as described above, but without the formation of a flexible reinforcement tube layer thereover. Optionally, the extruded thermoplastic tube may have a greater wall thickness over the segment which eventually forms the inner tubular wall in order to enhance its mechanical strength. The thickness of the portion which eventually forms the outer tubular wall may be reduced by axially stretching that segment. Such wall thickness reduction is particularly desirable for the region which will eventually form the inflation balloon where a greater degree of flexibility or slackness is required.

The catheter 100 includes inner tubular wall 102 and outer tubular wall 104, with dilation balloon 106 being formed by expansion of the distal end of the outer tubular wall. An annular lumen 107 will usually be left in the region between walls 104 and 106 extending from the balloon back to the proximate end (not shown), although separate inflation lumens may be provided within the inner tubular wall or outer tubular wall, as described above.

The structure of the present invention is particularly advantageous in that it allows construction from high temperature polymers, particularly halocarbon polymers, more particularly fluorocarbon polymers which are not amenable to normal sealing techniques. As the structure of the present invention does not require sealing, the choice of thermoplastic construction material is substantially unrestricted. Fluorocarbon polymers, such as polytetrafluoroethylene, fluorinated ethylene propylene polymers, chlorotrifluoroethylene polymers, polyvinylidene fluoride, and hexafluoropropylene polymers, are particularly suitable for the construction of thermal ablation balloon catheters, as described below, which require high temperature operation.

An optical waveguide 110 is provided in the catheter 100 of FIG. 9. The optical waveguide 110 allows the transmission of laser energy to the inflation medium within the balloon 106, allowing heating thereof. Optionally, means for dispersing the thermal energy within the balloon volume, or multiple waveguides, may be provided to enhance the heating uniformity. Usually, an opaque inflation medium will be employed and the wavelength of the laser energy will be selected to enhance the energy absorption and heating of the inflation medium. By thus heating the inflation medium, convective heating of the stenotic material may be achieved. Alternatively, the wavelength of the laser energy may be selected to enhance transmission through both the inflation medium and the balloon wall, allowing direct radiative heating and ablation of the material obstructing the blood vessle. Particularly suitable laser types for both conductive and radiative heating are set forth in the following list.

| Laser Type | Wave Length | Effect |
| --- | --- | --- |
| Carbon Dioxide | 10,600 nm | Absorbed by inflation medium including water, saline, with or without contrast agents. |
| Argon | 488–514 nm | Absorbed by pigmented tissues, hemoglobin, myoglobin, and colored inflation medium, particularly red-orange. |
| Nd-YAG (neodymium-yttrium aluminum garnet) | 1060 nm | Absorbed by vessel wall and proteins. |
| Excimer | 194–309 nm | Very high absorption by proteins and lipids in atherosclerotic tissue, with minimum penetration depth. |
| Tunable dye | 330–1250 nm | Can selectively duplicate effect of argon, excimer, and Nd-YAG lasers. |

Referring in particular to FIG. 10B, it will sometimes be desirable to provide a thinned region 120 in the outer tubular wall 104 defining the inflation balloon 106. Such reduced wall thickness will enhance the heat transfer across that portion of the wall, allowing the thermal treatment to be more specifically directed at (localized) particular circumferential regions of the stenosis. (FIG. 10A shows the same cross-sectional view as 10B with an unthinned wall region 104).

Figure 11:
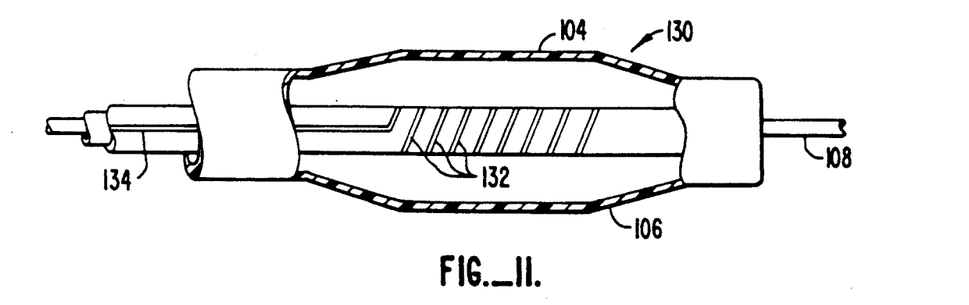
FIG. 11 is similar to FIG. 9, but illustrates an electrical resistance heater for the inflation medium.

Referring now to FIG. 11, an alternative catheter embodiment 130 is illustrated. The catheter 130 is substantially similar to catheter 100, except that an electrical resistance heating element 132, typically a wire coiled around the inner tubular wall 102, is provided in place of the optical waveguide 110. In this way, electrical heating of the inflation medium within the balloon 106 may be utilized. Wire connections 134 may be provided from the heating element 32 to the proximate end (not illustrated) of the catheter for connection to an appropriate power supply. Thermocouples or thermistors (not illustrated) within the balloon 106 may be provided to monitor and control the temperature of the inflation medium.

Figure 12:
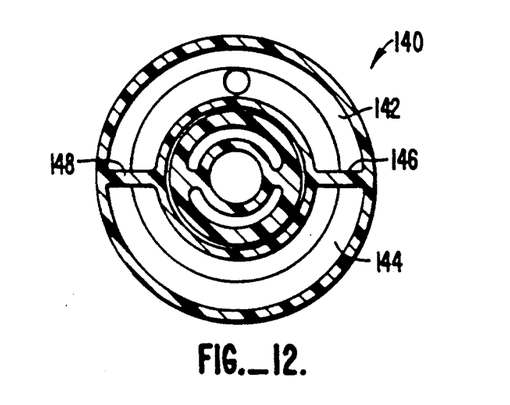
FIG. 12 is a cross-sectional view of a dilation balloon having two separate inflation compartments.

Referring now to FIG. 12, a catheter embodiment 140 having multiple compartments within the inflation balloon is illustrated. Such a multiple compartment construction may be provided by involution of a multilumen thermoplastic tube, by the techniques described above. As illustrated in FIG. 12, a dual-lumen tube was utilized, resulting in compartments 142 and 144 which are separated by walls 146 and 148. Such multiple compartment constructions are useful as they allow selective heating of one or more of the compartments, while leaving the other compartments substantially unheated. Such localized heating is useful when it is desired to direct the heat at particular circumferential segments of the stenosis.

For performing thermal ablation angioplasty, the balloon catheters of the present invention will be inserted into the patient's vascular system by conventional techniques, typically employing guidewires 108. Once the catheter balloons are located within the region of stenosis, the balloons will be dilated, typically at a pressure in the range from about 10 to 200 psi, more typically in the range from about 25 to 120 psi. After inflation, the inflation medium within the balloon will be heated, typically to a temperature in the range from about 120° to 200° C., more typically in the range from about 130° to 180° C., for a time sufficient to cause dehydration, cellular shrinkage, and ultimately vaporization or ablation of the stenotic material, usually in the range from about 5 to 60 seconds more usually being at least about 10 seconds at lower temperatures near 120° C. and at least about 5 seconds at higher emperatures near 180° C. The continuous nature of the sheath defining the inflation balloon is critical in allowing operation at such elevated temperatures.

Thermal ablation angioplasty utilizing heated balloon catheters, as described herein, is an improvement over both conventional balloon angioplasty and thermal ablation techniques employing direct laser energy and heated metallic caps. Balloon thermal ablation does not have a significant risk of restenosis and abrupt closure, as suffered by conventional balloon angioplasty. Moreover, the use of the heated balloon does not result in a substantial risk of puncture as with direct laser ablation and provides a much more efficient degree of heat transfer than with heated metal cap catheters.

Although the foregoing invention has been described in some detail by way of illustration and example for purposes of clarity of understanding, it will be obvious that certain changes and modifications may be practiced within the scope of the appended claims.

What is claimed is:

1. A vascular dilation catheter comprising:
   an inner and an outer tubular wall formed as a seamless, involuted structure having proximate and distal ends;
   a dilation balloon defined by an expanded portion of the outer tubular wall at the distal end of the seamless, involuted structure so that the balloon has a substantially cylindrical outer tubular wall proximate the distal end;
   means for directing an inflation medium from the proximate end of the structure to the dilation balloon; and
   a flexible reinforcement tube disposed around the inner tubular wall and extending substantially over the entire length of the catheter.

2. A vascular dilation catheter as in claim 1, wherein the flexible reinforcement tube is composed of a material selected from the group consisting of nylon, polyethylenes, polyolefins, polyvinylchlorides, and polyurethanes.

3. A vascular dilation catheter as in claim 1, wherein the inner and outer tubular walls are composed of a material selected from the group consisting of cross-linked polyolefins and halocarbon polymers.

4. A vascular dilation catheter as in claim 1, having a length in the range from about 40 to 150 cm, a central lumen diameter in the range from about 0.25 to 1.5 mm., an outside tube diameter in the range from about 0.5 to 2 mm.

5. A vascular dilation catheter as in claim 1, wherein the dilation balloon has an outside diameter in the range from about 1 to 30 mm and a length in the range from about 1 to 20 cm.

6. A vascular dilation catheter as in claim 1, wherein the means for directing an inflation medium is defined by an annular lumen between the inner and outer tubular wall, which lumen extends from the dilation balloon to the proximate end of the catheter.

7. A vascular dilation catheter as in claim 1, wherein the means for directing an inflation medium is defined by one or more axial lumens extending through the inner tubular wall, with said outer tubular wall conforming to the inner tubular wall.

8. A vascular dilation catheter as in claim 1, wherein the means for directing an inflation medium is defined by one or more axial lumens extending through the outer tubular wall, with said outer tubular wall conforming to the inner tubular wall.

9. A vascular dilation catheter as in claim 1, wherein the inner wall is reinforced in the region of the balloon.

10. A vascular dilation catheter comprising:
    a flexible tube having proximate and distal ends and an axial lumen extending between said proximate and distal ends;
    a flexible sheath extending through the lumen from the proximate end to the distal end, folding back over the exterior of the tube at the distal end, and extending over the exterior to the proximate end to form an annular space between the exterior of the tube and the sheath, said annular space including a first enlarged region proximate the distal end which defines a dilation balloon and a second narrower region between the first region and the proximate end which defines a conduit for directing inflation medium to the dilation balloon.

11. A vascular dilation catheter as in claim 10, further including a fitting mounted at the proximate end of the catheter.

12. A vascular dilation catheter as in claim 10, wherein the flexible tube is a thermoplastic material extruded over the portion of the sheath which extends through the lumen of the flexible tube.

13. A vascular dilation catheter as in claim 12, wherein the thermoplastic material is selected from the group consisting of nylon, polyethylenes, polyolefins, polyvinylchlorides, and polyurethanes.

14. A vascular dilation catheter as in claim 10, wherein the sheath is composed of a cross-linked polyolefin or a halocarbon polymer.

15. A vascular dilation catheter as in claim 10, having a length in the range from about 40 to 150 cm, a central lumen diameter in the range from about 0.25 to 1.5 mm., an outside tube diameter in the range from about 0.5 to 2 mm.

16. A vascular dilation catheter as in claim 10, wherein the dilation balloon has an outside diameter in the range from about 1 to 30 mm. and a length in the range from about 1 to 20 cm.

17. A vascular dilation catheter as in claim 10, wherein the flexible tube is a laminate construction of at least two materials.

18. A vascular dilation catheter as in claim 10, wherein the flexible tube comprises a polyurethane and the sheath comprises a cross-linked polyolefin or a halocarbon polymer.

19. A vascular catheter comprising:
    an inner and outer tubular wall formed as a seamless, involuted structure having proximate and distal ends;
    a dilation balloon defined by an expanded portion of the outer tubular wall at the distal end of the seamless, involuted structure;
    means for dividing the internal volume of the balloon into a plurality of separate compartments;
    means for directing an inflation medium from the proximate end of the structure to the dilation balloon; and
    means for heating inflation medium within the dilation balloon.

20. A vascular catheter as in claim 19, wherein the means for heating inflation medium selectively heats inflation medium in one or more of the separate compartments.

21. A method for ablating stenosis within a blood vessel, said method comprising:
    introducing a balloon dilation catheter into the blood vessel so that the balloon lies adjacent the stenosis, wherein the dilation balloon is divided into separate compartments;
    inflating the balloon;
    heating the inflation medium within selected ones of said compartments within the balloon to a preselected minimum temperature; and
    leaving the balloon in contact with the stenosis for a time sufficient to achieve ablation.

* * * * *